US010758838B2

(12) United States Patent
Schmidt et al.

(10) Patent No.: US 10,758,838 B2
(45) Date of Patent: Sep. 1, 2020

(54) PROCESS FOR REMOVING IMPURITIES FROM ACETIC ACID

(71) Applicant: SABIC Global Technologies B.V., Bergen op Zoom (NL)

(72) Inventors: Roland Schmidt, Wiehl (DE); Sebastiano Licciulli, Riyadh (SA); Shahid Azam, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 112 days.

(21) Appl. No.: 15/553,761

(22) PCT Filed: Feb. 23, 2016

(86) PCT No.: PCT/IB2016/050979
§ 371 (c)(1),
(2) Date: Aug. 25, 2017

(87) PCT Pub. No.: WO2016/135630
PCT Pub. Date: Sep. 1, 2016

(65) Prior Publication Data
US 2018/0021692 A1    Jan. 25, 2018

Related U.S. Application Data

(60) Provisional application No. 62/120,684, filed on Feb. 25, 2015.

(51) Int. Cl.
*B01D 3/00* (2006.01)
*B01D 5/00* (2006.01)
(Continued)

(52) U.S. Cl.
CPC ........... *B01D 3/009* (2013.01); *B01D 5/0036* (2013.01); *C07C 51/487* (2013.01); *C07C 53/08* (2013.01);
(Continued)

(58) Field of Classification Search
CPC .... B01D 3/009; B01D 5/0036; C07C 51/487; C07C 53/08; C07C 57/03; C01D 13/00; C01G 45/1214; Y02P 20/127
See application file for complete search history.

(56) References Cited

U.S. PATENT DOCUMENTS 2,893,923 A * 7/1959 Luke, Jr. ................. C07C 53/08
203/31
3,709,795 A * 1/1973 Singleton .............. C07C 51/487
203/31
(Continued)

FOREIGN PATENT DOCUMENTS

CN       1634842    *  7/2005  ............. C07C 51/47
DE   2618021 A1 * 11/1977  ........... C07C 51/487
(Continued)

OTHER PUBLICATIONS

Non-Patent Literature filed on Aug. 25, 2017 (Espacenet machine translation of Muenster) (Year: 1977).*
(Continued)

*Primary Examiner* — Jonathan Miller
*Assistant Examiner* — Gabriel E Gitman
(74) *Attorney, Agent, or Firm* — Norton Rose Fulbright US LLP

(57) ABSTRACT

A process of purifying acetic acid is provided. The process includes feeding a stream of acetic acid into a distillation column and distilling acetic acid in the presence of an oxidizing agent in the distillation column, to oxidize oxidizable impurities in the acetic acid, wherein the oxidizing agent is an oxidant capable of cleaving C=C bonds. The process further includes removing a distilled acetic acid stream from the distillation column. Further processes for purifying acetic acid and systems for purifying acetic acid are also provided.

15 Claims, 1 Drawing Sheet

(51) Int. Cl.

| | | |
|---|---|---|
| *C07C 51/487* | (2006.01) | |
| *C07C 53/08* | (2006.01) | |
| *B01D 3/14* | (2006.01) | |
| *C01D 13/00* | (2006.01) | |
| *C01G 45/12* | (2006.01) | |
| *C07C 57/03* | (2006.01) | |

(52) U.S. Cl.
CPC ............. *B01D 3/146* (2013.01); *C01D 13/00* (2013.01); *C01G 45/1214* (2013.01); *C07C 57/03* (2013.01); *Y02P 20/127* (2015.11)

(56) References Cited

U.S. PATENT DOCUMENTS

| | | | | |
|---|---|---|---|---|
| 3,878,241 A | * | 4/1975 | Muller | C07C 51/44 203/16 |
| 4,061,546 A | * | 12/1977 | Singleton | B01D 3/34 203/31 |
| 4,268,362 A | * | 5/1981 | Ogawa | C07C 51/44 203/28 |
| 4,380,663 A | | 4/1983 | Roscher et al. | |
| 5,169,982 A | | 12/1992 | Heinz et al. | |
| 5,306,398 A | | 4/1994 | Seidel et al. | |
| 5,387,713 A | | 2/1995 | Cook et al. | |
| 5,529,697 A | * | 6/1996 | Braasch | C02F 1/5236 210/710 |
| 6,667,418 B2 | * | 12/2003 | Broussard | C07C 51/12 562/519 |
| 2003/0166668 A1 | * | 9/2003 | Zandt | C07D 213/61 514/265.1 |
| 2009/0156859 A1 | * | 6/2009 | Scates | C07C 51/47 562/517 |
| 2013/0184491 A1 | * | 7/2013 | Le Berre | C07C 51/12 562/519 |
| 2015/0025270 A1 | * | 1/2015 | Shimizu | C07D 51/44 562/519 |

FOREIGN PATENT DOCUMENTS

| | | | | |
|---|---|---|---|---|
| DE | 2618021 A1 | | 11/1977 | |
| EP | 0322215 A1 | | 6/1989 | |
| EP | 0372993 A1 | | 6/1990 | |
| EP | 0494527 A1 | | 7/1992 | |
| EP | 0571163 A1 | | 11/1993 | |
| FR | 1083772 | * | 1/1955 | ........... C07C 51/487 |
| FR | 1083772 | | 1/1955 | |
| JP | S51136613 A | | 11/1976 | |
| JP | S5365814 A | | 6/1978 | |
| JP | S5564545 A | | 5/1980 | |
| JP | S6156151 A | | 3/1986 | |
| JP | H04338357 A | | 11/1992 | |
| JP | WO2014199593 A1 | * | 12/2014 | ............. B01J 39/05 |
| SU | 1198057 A1 | | 12/1985 | |
| WO | 2007120554 A2 | | 10/2007 | |
| WO | WO2014115826 A1 | * | 7/2014 | ............. C07C 51/44 |
| WO | WO2014199593 A1 | * | 12/2014 | ............. B01J 39/05 |

OTHER PUBLICATIONS

CN1634842A_ENG (Patentscope machine translation of Yan) (Year: 2005).*
Richardson, J.F. Harker, J.H. Backhurst, J.R.. (2002). Coulson and Richardson's Chemical Engineering vol. 2—Particle Technology and Separation Processes (5th Edition)—11.4.1 The Fractionating Process. Elsevier. (Year: 2002).*
PubChem. Densities of potassium permanganate, acetic acid, and water. (Year: 2019).*
WO2014115826A1_ENG (Espacenet machine translation of Miura) (Year: 2014).*
Agreda, V. H. (1992). Acetic acid and its derivatives. CRC Press. Accessed on Jan. 7, 2020 at Google Books. p. 31 (Year: 1992).*
Caballero, Jose and Grossman, Ignacio. (2014). Distillation: Fundamentals and Principles—Optimization Background. Chapter 11: Optimization of Distillation Processes. Editors: Górak, Andrzej; Sorensen, Eva. Elsevier (Year: 2014).*
WO2014199593A1_ENG (Espacenet machine translation of Zhixiong) (Year: 2014).*
French Patent No. 1083772; Date of Publication: Jan. 12, 1955; Machine Translation, 4 pages.
German Patent No. 2618021; Date of Publication: Nov. 10, 1977; Machine Translation, 16 pages.
International Search Report for International Application No. PCT/IB2016/050979; dated Jun. 3, 2016; 7 pages.
Japanese Publication No. H04338357; Date of Publication: Nov. 25, 1992; Abstract Only, 1 page.
Japanese Publication No. S50121213; Date of Publication: Sep. 23, 1975; English Translation, 8 pages.
Japanese Publication No. S51136613; Date of Publication: Nov. 26, 1976; Abstract Only, 1 page.
Japanese Publication No. S5365814; Date of Publication: Jun. 12, 1978; Abstract Only, 1 page.
Japanese Publication No. S5564545; Date of Publication: May 15, 1980; Abstract Only, 1 page.
Japanese Publication No. S6156151; Date of Publication: Mar. 20, 1986; Abstract Only, 1 page.
Union of Soviet Socialist Republics Publication No. 1198057; Date of Publication: Dec. 15, 1985; Abstract Only, 2 pages.
Written Opinion of the International Search Report for International Application No. PCT/IB2016/050979; dated Jun. 3, 2016; 10 pages.

* cited by examiner

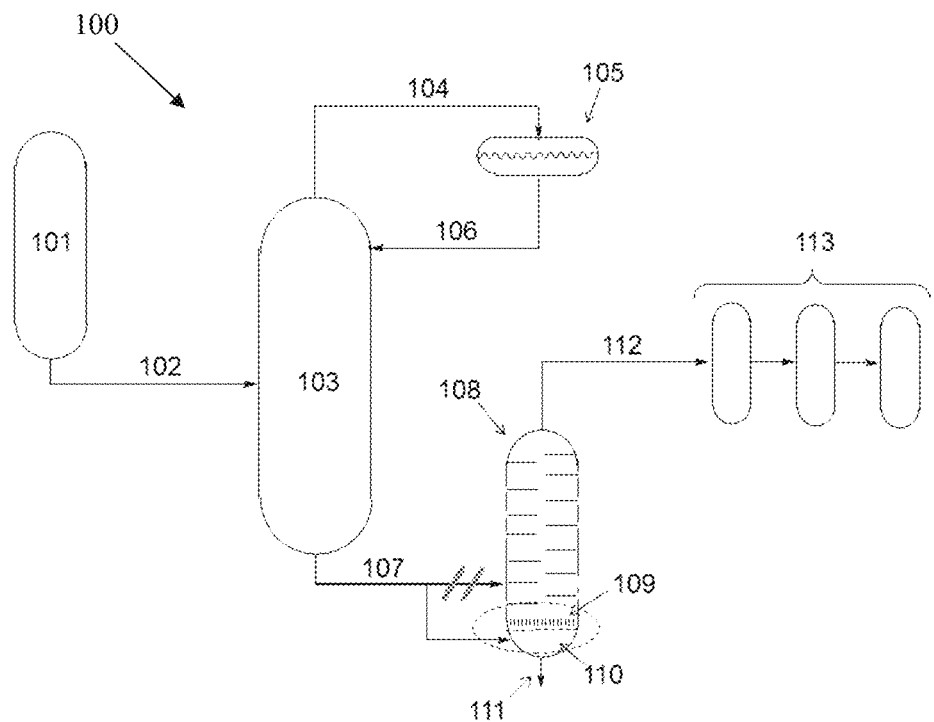

PROCESS FOR REMOVING IMPURITIES FROM ACETIC ACID

CROSS REFERENCE TO RELATED APPLICATIONS

This application is a 371 of International Application No. PCT/IB2016/050979, filed Feb. 23, 2016, which claims priority to U.S. Application No. 62/120,684, filed Feb. 25, 2015, both of which are incorporated herein by reference in their entirety.

TECHNICAL FIELD

The presently disclosed subject matter relates to processes and systems for purifying acetic acid.

BACKGROUND

Acetic acid is a widely used chemical. Acetic acid has the chemical formula $CH_3CO_2H$ and is sometimes also known as ethanoic acid or methanecarboxylic acid. It is commonly abbreviated as $MeCO_2H$, MeCOOH, AcOH, and AA. Acetic acid is a major feedstock in the chemical and polymer industries. As the key component of vinegar, acetic acid also has many applications in food.

Acetic acid can contain various impurities, which can include aldehydes (e.g., acetaldehyde and formaldehyde), formic acid, acrylic acid, water, inorganic and organic salts, and various other compounds. The levels of impurities can depend on the method of production of acetic acid. One commonly used test of the purity of acetic acid is the permanganate test. The permanganate test measures oxidizable impurities present in acetic acid. A quantity of permanganate, e.g., a standardized solution, can be added to a concentrated sample of acetic acid, creating a colored solution. Fading of the characteristic pink color of permanganate indicates consumption of permanganate through reaction with oxidizable impurities. The time over which the pink color of permanganate survives can be described as the "permanganate time," and samples of acetic acid with long permanganate time can be inferred to contain low levels of oxidizable impurities. Acetic acid that passes the permanganate test (i.e., acetic acid with low levels of oxidizable impurities) can be particularly valuable in applications that demand high purity acetic acid.

Industrially produced acetic acid often contains oxidizable impurities and fails the permanganate test. Various processes and systems for purifying acetic acid are described in the literature. However, there remains a need in the art for improved processes and systems for purification of acetic acid, including processes and systems capable of removing oxidizable impurities from acetic acid.

SUMMARY

The presently disclosed subject matter provides processes and systems for purifying acetic acid.

A process for purifying acetic acid comprises: feeding a stream of acetic acid into a distillation column; distilling acetic acid in the presence of an oxidizing agent in the distillation column, to oxidize oxidizable impurities in the acetic acid, wherein the oxidizing agent is capable of cleaving C=C bonds; and removing a distilled acetic acid stream from the distillation column.

A process for purifying acetic acid comprises: feeding a stream of acetic acid into a distillation column, wherein: the distillation column comprises: a top and a bottom; and a sump at the bottom of the distillation column; and wherein the stream of acetic acid is fed into the distillation column at or near the bottom of the distillation column; and distilling acetic acid in the presence of an oxidizing agent, wherein the oxidizing agent is positioned at or near the bottom of the distillation column.

A system for purifying acetic acid, comprises: a distillation column, wherein the distillation column comprises: a top and a bottom; and a sump at the bottom of the distillation column; an oxidizing agent positioned at or near the bottom of the distillation column; and an acetic acid feed line to feed acetic acid into the distillation column positioned at or near the bottom of the distillation column.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The FIGURE is a schematic diagram depicting an exemplary system for purifying acetic acid in accordance with one non-limiting embodiment of the disclosed subject matter.

DETAILED DESCRIPTION

The presently disclosed subject matter provides processes and systems for purifying acetic acid. Acetic acid can be purified to remove various impurities, and overall product quality of industrial acetic acid can be improved.

In one embodiment, a non-limiting exemplary process for purifying acetic acid includes feeding a stream of acetic acid into a distillation column. The process further includes distilling acetic acid in the presence of an oxidizing agent in the distillation column, to oxidize oxidizable impurities in the acetic acid, wherein the oxidizing agent is capable of cleaving C=C bonds. The process further includes removing a distilled acetic acid stream from the distillation column.

In certain embodiments, the oxidizable impurities can include one or more α,β-unsaturated carbonyl compounds. The one or more α,β-unsaturated carbonyl compounds can include one or more α,β-unsaturated carboxylic acids. The one or more α,β-unsaturated carboxylic acids can include acrylic acid.

In certain embodiments, the oxidizing agent can include potassium permanganate. The potassium permanganate can include an aqueous solution of potassium permanganate. The potassium permanganate can include potassium permanganate on a solid support. The solid support can be silica.

In certain embodiments, the distillation column can include a top and a bottom, and the oxidizing agent can be positioned at or near the bottom of the distillation column. In certain embodiments, the distillation column can include a sump at the bottom of the distillation column and the oxidizing agent can be positioned in the sump.

In certain embodiments, the process can further include feeding the distilled acetic acid stream through a sorbent phase capable of removing at least one impurity selected from the group consisting of water, formic acid, and aldehydes.

In certain embodiments, the process can further include additional distillation of acetic acid through one or more additional distillation columns.

In another embodiment, a non-limiting exemplary process for purifying acetic acid includes feeding a stream of acetic acid into a distillation column, wherein the distillation column includes a top and a bottom and a sump at the bottom of the distillation column, and wherein acetic acid is fed into the distillation column at or near the bottom of the distillation column. The process further includes distilling acetic acid in the presence of an oxidizing agent, wherein the oxidizing agent is positioned at or near the bottom of the distillation column.

In one embodiment, a non-limiting exemplary system for purifying acetic acid includes a distillation column, wherein the distillation column includes a top and a bottom and a sump at the bottom of the distillation column. The system further includes an oxidizing agent positioned at or near the bottom of the distillation column and an acetic acid feed line to feed acetic acid into the distillation column positioned at or near the bottom of the distillation column.

In certain embodiments, the oxidizing agent can be positioned on a tray near the bottom of the distillation column. In certain embodiments, the oxidizing agent can be positioned in the sump at the bottom of the distillation column. In certain embodiments, the acetic acid feed line can be positioned to feed acetic acid into the sump at the bottom of the distillation column.

The term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In certain embodiments, non-limiting exemplary processes and systems for purifying acetic acid include feeding a stream of acetic acid into a distillation column. The stream of acetic acid can be fed from an acetic acid source. In certain embodiments, the acetic acid source can be an existing facility for production of acetic acid, e.g., an industrial facility. The acetic acid source can feed a stream of acetic acid that contains various impurities, e.g., water, inorganic and organic salts, and/or oxidizable impurities. In this way, the acetic acid source can feed a stream of acetic acid that is of relatively low purity.

Oxidizing Agents

Oxidizing agents are also known as oxidants and oxidizers. By way of non-limiting example, oxidizing agents can generally include oxygen ($O_2$), ozone ($O_3$), peroxides (e.g., hydrogen peroxide ($H_2O_2$)), peracids (also known as peroxy acids or peroxyacids, e.g., peracetic acid), peroxyesters (also known as peroxy esters), nitric acid ($HNO_3$), nitrates (e.g., sodium nitrate ($NaNO_3$)), sulfuric acid ($H_2SO_4$), peroxysulfates (e.g., potassium peroxomonosulfate (OXONE™) and tetrabutylammonium peroxomonosulfate (OXONE™ tetrabutylammonium salt)), halogens (e.g., $F_2$, $Cl_2$, $Br_2$, and $I_2$), hypochlorites, chlorites, chlorates, perchlorates, hypobromites, bromites, bromates, perbromates, hypoiodites, iodites, iodates, periodates, permanganates, Cr(VI) complexes (e.g., $CrO_3$), and perborates (e.g., $NaBO_3$).

Certain oxidizing agents are capable of cleaving C=C bonds. C=C bonds are carbon-carbon double bonds. By way of non-limiting example, the oxidizing agent capable of cleaving C=C bonds can include permanganate salts, e.g., potassium permanganate ($KMnO_4$), ammonium permanganate ($NH_4MnO_4$), tetraalkylammonium permanganate salts (e.g., tetrabutylammonium permanganate), calcium permanganate ($Ca(MnO_4)_2$), and sodium permanganate ($NaMnO_4$). The oxidizing agent capable of cleaving C=C bonds can also include ozone ($O_3$), periodate salts (e.g., sodium periodate ($NaIO_4$) and potassium periodate ($KIO_4$)), perchlorate salts (e.g., sodium perchlorate ($NaClO_4$)), chlorate salts (e.g., sodium chlorate ($NaClO_3$)), peroxides (e.g., hydrogen peroxide ($H_2O_2$), and peracids (e.g., peracetic acid ($CH_3CO_3H$). In certain non-limiting embodiments, the oxidizing agent capable of cleaving C=C bonds can include a transition metal complex, e.g., a complex of Fe, Mo, Co, Cr, V, Cu, Ag, W, Ta, Os, Rh, Ru, or Re. In certain embodiments, the transition metal complex can be used catalytically. By way of non-limiting example, transition metal complexes that can be used catalytically can include [SiRu($H_2O$)—$W_{11}O_{39}$](($C_6H_{13})_4N)_5$ (a ruthenium polyoxometalate, which can be used in conjunction with a periodate, e.g., $NaIO_4$), [($PW_4O_{24}$)]($C_5H_5N$—$C_{16}H_{33})_3$ (a peroxo form of phosphotungstic acid, which can be used in conjunction with a peroxide, e.g., $H_2O_2$), [cis-Ru(II)(dmp)$_2$($H_2O)_2$](PF$_6)_2$, wherein dmp is 2,9-dimethyl-1,10-phenanthroline (which can be used in conjunction with a peroxide, e.g., $H_2O_2$), [OsO(N-aryl-1,2-arylenediamine)$_2$], and methyltrioxorhenium (MTO).

The oxidizing agent can include oxidizing agents in gaseous, liquid, and/or solid forms. Gaseous oxidizing agents can include oxygen and ozone. Liquid oxidizing agents can include solutions of an oxidizing agent in a solvent, e.g., water and/or acetic acid. Liquid oxidizing agents can serve as homogeneous oxidizing agents. A liquid oxidizing agent can be used in such a way that acetic acid and impurities can mix with, diffuse through, or bubble through the liquid oxidizing agent. For example, in certain non-limiting embodiments, a stream of acetic acid containing oxidizable impurities can be mixed with an aqueous solution, e.g., an aqueous solution of potassium permanganate.

Solid oxidizing agents can include oxidizing agents on a solid support or solid carrier. Such oxidizing agents on a solid support or solid carrier can include oxidizing agents adsorbed on the solid support or solid carrier. Oxidizing agents on a solid support or solid carrier can serve as heterogeneous oxidizing agents. Examples of solid supports and solid carriers used to prepare solid oxidizing agents can include various metal salts, metalloid oxides, and metal oxides, e.g., titanium oxide, zirconium oxide, silica (silicon oxide), alumina (aluminum oxide), magnesium oxide, and magnesium chloride. In certain embodiments, the solid support or solid carrier can be chosen for its high surface area. The oxidizing agents on a solid support or solid carrier can react with oxidizable impurities in the gas, liquid, or solid phase.

Oxidizing agents in one phase (gaseous, liquid, or solid) can be used in conjunction with one or more additional oxidizing agents in other phases. For example, solid oxidizing agents can be used in conjunction with liquid and/or gaseous oxidizing agents. For example, in certain non-limiting embodiments, an oxidizing agent on a solid support can be used in conjunction with a gaseous oxidant, e.g., oxygen or ozone.

Non-limiting exemplary processes and systems for purifying acetic acid include distilling acetic acid in the presence of an oxidizing agent in a distillation column, to oxidize oxidizable impurities in the acetic acid. The oxidizing agent can be an oxidizing agent capable of cleaving C=C bonds. The processes and systems can further include removing a distilled acetic acid stream from the distillation column. In certain embodiments, the oxidizing agent can be potassium permanganate. The potassium permanganate can include an aqueous solution of potassium permanganate. The potassium permanganate can include potassium permanganate adsorbed on a solid support. The solid support can be silica.

The amount of oxidizing agent used can be a stoichiometric amount with respect to the amount of oxidizable impurities in the acetic acid. That is, the number of moles of oxidizing agent used can be proportional to the number of moles of oxidizable impurities in the acetic acid. The amount of oxidizing agent used can be a super-stoichiometric amount. That is, an excess of oxidizing agent can be used.

Impurities

Impurities in acetic acid can include aldehydes (e.g., acetaldehyde and formaldehyde), formic acid, acrylic acid, water, inorganic and organic salts, and various other compounds. Some of the impurities in acetic acid can include oxidizable impurities. Oxidizable impurities can include aldehydes (e.g., acetaldehyde and formaldehyde). In certain embodiments, the oxidizable impurities can include one or more α,β-unsaturated carbonyl compounds. The one or more α,β-unsaturated carbonyl compounds can include one or more α,β-unsaturated carboxylic acids. The one or more α,β-unsaturated carboxylic acids can include acrylic acid, methacrylic acid, 2-butenoic acid (cis and/or trans), 4-methyl-2-pentenoic acid (cis and/or trans), and 5-methyl-2-hexenoic acid (cis and/or trans). The one or more α,β-unsaturated carbonyl compounds can also include one or more α,β-unsaturated aldehydes. The one or more α,β-unsaturated aldehydes can include acrolein, methacrolein, 2-butenal (cis and/or trans), 4-methyl-2-pentenal (cis and/or trans), and 5-methyl-2-hexenal (cis and/or trans).

When acetic acid is distilled in the presence of an oxidizing agent, oxidizable impurities in the acetic acid can react with the oxidizing agent to form oxidized impurities. The oxidized impurities can have boiling points substantially higher than those of their precursors (the oxidizable impurities) and also substantially higher than that of acetic acid. The oxidized impurities can have substantially lower volatility than acetic acid. In this way, acetic acid can be distilled while the oxidized impurities do not distill with acetic acid, producing a purified distilled acetic acid.

As noted above, the process for purifying acetic acid can include distilling acetic acid in the presence of an oxidizing agent capable of cleaving C=C bonds. Such a process can be useful in purifying acetic acid that is contaminated with impurities containing C=C bonds, e.g., α,β-unsaturated carbonyl compounds, e.g., acrylic acid. Existing processes and systems for purifying acetic acid can emphasize treating acetic acid with an oxidizing agent to remove acetaldehyde, formaldehyde, and other aldehyde impurities. Such processes and systems can fail to remove certain impurities containing C=C bonds, e.g., α,β-unsaturated carbonyl compounds, e.g., acrylic acid. Use of an oxidizing agent capable of cleaving C=C bonds can convert α,β-unsaturated carbonyl compounds, e.g., acrylic acid, into oxidized impurities of low volatility, which can then be separated from acetic acid to generate acetic acid of high purity.

Processes and Systems for Purifying Acetic Acid

In certain embodiments, the distillation column can include a top and a bottom, and the oxidizing agent can be positioned at or near the bottom of the distillation column. For example, in certain non-limiting embodiments, the oxidizing agent near the bottom of the distillation column can be positioned within about 5%, within about 10%, within about 15%, within about 20%, or within about 25% of the distance from the bottom of the distillation column to the top of the distillation column. In certain embodiments, the distillation column can include a sump at the bottom of the distillation column, and the oxidizing agent can be positioned in the sump.

The distillation of acetic acid can be conducted under conditions known in the art. For example, in certain non-limiting embodiments, acetic acid can be distilled from a mixture of acetic acid and water, e.g., an aqueous solution of acetic acid. The aqueous solution of acetic acid can have an acidic pH. In certain embodiments, acetic acid can be distilled at a temperature of about 50° C. to about 200° C. In certain embodiments, acetic acid can be distilled at a temperature of about 90° C. to about 150° C., for example at about 100° C., about 110° C., about 120° C., or about 130° C. The distillation can be conducted at various pressures, including reduced pressures, atmospheric pressure, or elevated pressures. In certain embodiments, distillation can be conducted at a reduced pressure, e.g., a pressure of less than 1 bar (100 kiloPascals (kPa), about 0.5 bar (about 50 kPa), about 0.3 bar (about 30 kPa), about 0.2 bar (about 20 kPa), about 0.1 bar (about 10 kPa), about 0.05 bar (about 5 kPa), about 0.03 bar (about 3 kPa), about 0.02 bar (about 2 kPa), about 0.01 bar (about 1 kPa), or less than 0.01 bar (about 1 kPa). Distillation can alternatively be conducted at an elevated pressure. For example, distillation can be conducted at a pressure between about 1 bar and about 4 bar (about 100 kPa and about 400 kPa), e.g., at about 1 bar (about 100 kPa), about 1.5 bar (about 150 kPa), about 2 bar (about 200 kPa), about 2.5 bar (about 250 kPa), about 3 bar (about 300 kPa), about 3.5 bar (about 350 kPa), or about 4 bar (about 400 kPa).

In certain embodiments, the processes and systems can further include feeding the distilled acetic acid stream through a sorbent phase capable of removing at least one impurity selected from water, and/or formic acid, and/or aldehydes. Acetic acid can be "polished," or further purified, by feeding through one or more sorbent phases. High purity acetic acid with low levels of impurities can obtained after passage through one or more sorbent phases. By way of non-limiting example, the sorbent can include a ROHM AND HAAS™ IRA sorbent, a ROHM AND HAAS™ XAD sorbent, a DOW™ XUS sorbent, or a combination comprising at least one of the foregoing.

In certain embodiments, the process can further include additional distillation of acetic acid through one or more additional distillation columns. In certain non-limiting embodiments, acetic acid can be distilled in a first distillation column to remove certain impurities and then further distilled in a second distillation column to remove additional impurities. In certain embodiments, the first distillation column can include an oxidizing agent. In certain embodiments, the second distillation column can include an oxidizing agent. In certain embodiments, the first and second distillation columns can both include an oxidizing agent. In certain embodiments, an oxidizing agent can be positioned between the first and second distillation columns. In certain embodiments, more than two distillation columns can be used in series, and one, two, or more of the columns can include an oxidizing agent.

In certain embodiments, non-limiting exemplary processes and systems for purifying acetic acid can include feeding a stream of acetic acid into a distillation column, wherein the distillation column includes a top and a bottom and a sump at the bottom of the distillation column, and wherein acetic acid is fed into the distillation column at or near the bottom of the distillation column. Acetic acid can be distilled in the presence of an oxidizing agent, and the oxidizing agent can be positioned at or near the bottom of the distillation column.

In certain embodiments, non-limiting exemplary processes and systems for purifying acetic acid can include a distillation column, wherein the distillation column includes a top and a bottom and a sump at the bottom of the distillation column. An oxidizing agent can be positioned at or near the bottom of the distillation column, and an acetic acid feed line to feed acetic acid into the distillation column can be positioned at or near the bottom of the distillation column.

In certain embodiments, the oxidizing agent can be positioned on a tray near the bottom of the distillation column. The tray can be a diffusible tray, i.e., a tray that allows acetic acid in liquid and/or gaseous form to contact the oxidizing agent and that allows oxidizable impurities in the acetic acid to react with oxidizing agent. In other embodiments, the oxidizing agent can be positioned in the sump at the bottom of the distillation column. In certain embodiments, oxidizing agents can be positioned both on a tray near the bottom of the distillation column and also in the sump at the bottom of the distillation column. In certain embodiments, the acetic acid feed line can be positioned to feed acetic acid into the sump at the bottom of the distillation column.

In certain embodiments, the oxidizing agent can be recharged. An oxidizing agent can be recharged by various techniques known in the art. For example, an oxidizing agent can be recharged by continuous addition of fresh oxidizing agent. By way of non-limiting example, fresh oxidizing agent can be added as portions of a solid oxidizing agent, as a solid dispersion of oxidizing agent on an inert bed, and/or as a concentrated solution of oxidizing agent in water or another solvent.

For the purpose of illustration and not limitation, the FIGURE is a schematic representation of an exemplary system for purifying acetic acid according to the disclosed subject matter. The system 100 can include an acetic acid source 101. As noted above, the acetic acid source 101 can be an existing facility for production of acetic acid (e.g., an acetic acid reactor). The acetic acid source 101 can be coupled to an acetic acid feed line 102, which can be further coupled to a first distillation column 103. The acetic acid feed line 102 can feed acetic acid into the first distillation column 103. The first distillation column 103 can optionally be coupled to a high outlet line 104 positioned at or near the top of the first distillation column 103. The high outlet line 104 can remove water ($H_2O$) and butyl acetate from the first distillation column 103 and transfer it to an azeotropic separator 105. The azeotropic separator 105 can remove water and return butyl acetate to the first distillation column 103 through a butyl acetate outlet line 106 that feeds butyl acetate back into the first distillation column 103.

The first distillation column 103 can be further coupled to a low outlet line 107 positioned at or near the bottom of the first distillation column 103. The low outlet line 107 can remove acetic acid from the first distillation column 103 and feed acetic acid into a second distillation column 108. The low outlet line 107 can be coupled to the second distillation column 108 such that the low outlet line 107 feeds acetic acid into the second distillation column 108 at or near the bottom of the second distillation column 108. The low outlet line 107 can optionally feed acetic acid into a sump 110 at the bottom of the second distillation column 108. The second distillation column 108 can include an oxidizing agent 109. The oxidizing agent 109 can be positioned at or near the bottom of the second distillation column 108. The oxidizing agent 109 can be positioned on a tray near the bottom of the second distillation column 108, as shown in the FIGURE. Alternatively or additionally, the oxidizing agent 109 can be placed in the sump 110.

The second distillation column 108 can be coupled to a heavies outlet line 111 positioned at or near the bottom of the second distillation column 108. The heavies outlet line 111 can remove "heavies," i.e., relatively non-volatile compounds with relatively high boiling points, from the second distillation column 108. The heavies outlet line 111 can remove oxidized impurities from the second distillation column 108. The heavies outlet line 111 can also remove inorganic and organic salts from the second distillation column 108. The second distillation column 108 can be further coupled to a purified acetic acid outlet line 112 positioned at or near the top of the second distillation column 108. The purified acetic acid outlet line 112 can remove purified acetic acid from the second distillation column 108 after it has distilled through the second distillation column 108. The purified acetic acid outlet line 112 can be further coupled to one or more sorbent phases 113. The sorbent phases 113 can be polishers. The sorbent phases 113 can further purify the purified acetic acid and provide acetic acid in high purity, with low levels of oxidizable impurities and other impurities. The sorbent phases 113 can include sorbent phases capable of removing water, formic acid, and/or aldehydes.

In certain embodiments, the exemplary system 100 can include one or more additional oxidizing agents. By way of non-limiting example, a heterogeneous oxidizing agent can be positioned between the acetic acid source 101 and the first distillation column 103, e.g., in acetic acid feed line 102. Additionally or alternatively, a heterogeneous oxidizing agent can be positioned between the first distillation column 103 and the second distillation column 108, e.g., in low outlet line 107. Additionally or alternatively, a heterogeneous oxidizing agent can be positioned between the second distillation column 108 and one or more sorbent phases 113, e.g., in purified acetic acid outlet line 112.

The exemplary system 100 of the presently disclosed subject matter can be operated in continuous, semi-continuous, or batch mode. The various sections of the system 100 can be operated simultaneously or, alternatively, can be operated separately.

The distillation columns 103, 108 can be constructed of any desirable materials such as, but not limited to, metals, alloys including steel, glass, enamels, ceramics, polymers, plastics, or a combination comprising at least one of the foregoing.

Thus the presently disclosed subject matter provides processes and systems for purifying acetic acid which can have advantages over certain existing processes and systems for purifying acetic acid. As noted above, in certain embodiments the presently disclosed subject matter provides processes and systems that can remove impurities containing C=C bonds, including α,β-unsaturated carbonyl compounds, e.g., acrylic acid, from acetic acid, whereas existing processes and systems for purifying acetic acid can emphasize treating acetic acid with an oxidizing agent to remove acetaldehyde, formaldehyde, and other aldehyde impurities without removing impurities containing C=C bonds.

As noted above, the presently disclosed subject matter can include positioning an oxidizing agent on a tray near the bottom of a distillation column or in a sump at the bottom of a distillation column. Acetic acid can be distilled in the distillation column. As noted above, α,β-unsaturated carbonyl compounds present in the acetic acid can be oxidized by the oxidizing agent to oxidized impurities that are heavies, i.e., relatively non-volatile compounds with relatively high boiling points. Because of their relatively high boiling points, the heavies can remain in solution rather than distilling with acetic acid. The heavies can then be conveniently removed from the bottom of the column through a heavies outlet line. For example, acrylic acid can be oxidized with an oxidizing agent to oxalic acid or a salt thereof, which can be removed through a heavies outlet line. In this way, α,β-unsaturated impurities can be efficiently removed from acetic acid.

In certain embodiments of the presently disclosed subject matter, acetic acid is purified by multiple means, e.g., by a first distillation, a second distillation in the presence of an oxidizing agent, and subsequent polishing by passage of the acetic through one or more sorbent phases. In this way, highly purified acetic acid can be obtained. The highly purified acetic acid can be of higher purity and quality than acetic acid obtained from existing purification processes and systems. The highly purified acetic can be capable of passing the permanganate test, and can be useful in various specialized applications requiring very low levels of oxidizable impurities.

The processes and systems disclosed herein include at least the following embodiments:

Embodiment 1

A process for purifying acetic acid, comprising: feeding a stream of acetic acid into a distillation column; distilling acetic acid in the presence of an oxidizing agent in the distillation column, to oxidize oxidizable impurities in the acetic acid, wherein the oxidizing agent is capable of cleaving C═C bonds; and removing a distilled acetic acid stream from the distillation column.

Embodiment 2

The process of claim 1, wherein the oxidizable impurities comprise one or more α,β-unsaturated carbonyl compounds.

Embodiment 3

The process of claim 2, wherein the one or more α,β-unsaturated carbonyl compounds comprise one or more α,β-unsaturated carboxylic acids.

Embodiment 4

The process of claim 2 or claim 3, wherein the one or more α,β-unsaturated carboxylic acids comprise acrylic acid.

Embodiment 5

The process of any of the preceding claims, wherein the distillation column comprises a top and a bottom and wherein the oxidizing agent is positioned at or near the bottom of the distillation column.

Embodiment 6

The process of claim 5, wherein the distillation column comprises a sump at the bottom of the distillation column and the oxidizing agent is positioned in the sump.

Embodiment 7

A process for purifying acetic acid, comprising: feeding a stream of acetic acid into a distillation column, wherein: the distillation column comprises: a top and a bottom; and a sump at the bottom of the distillation column; and wherein the stream of acetic acid is fed into the distillation column at or near the bottom of the distillation column; and distilling acetic acid in the presence of an oxidizing agent, wherein the oxidizing agent is positioned at or near the bottom of the distillation column.

Embodiment 8

The process of any of the preceding claims, wherein the oxidizing agent comprises potassium permanganate.

Embodiment 9

The process of claim 8, wherein the potassium permanganate comprises an aqueous solution of potassium permanganate.

Embodiment 10

The process of claim 8 or claim 9, wherein the potassium permanganate comprises potassium permanganate on a solid support.

Embodiment 11

The process of claim 10, wherein the solid support is silica.

Embodiment 12

The process of any of the preceding claims, wherein the process further comprises feeding the distilled acetic acid stream through a sorbent phase capable of removing at least one impurity selected from water, or formic acid, or aldehydes.

Embodiment 13

The process of any of the preceding claims, wherein the process further comprises additional distillation of acetic acid through one or more additional distillation columns.

Embodiment 14

A system for purifying acetic acid, comprising: a distillation column, wherein the distillation column comprises: a top and a bottom; and a sump at the bottom of the distillation column; an oxidizing agent positioned at or near the bottom of the distillation column; and an acetic acid feed line to feed acetic acid into the distillation column positioned at or near the bottom of the distillation column.

Embodiment 15

The system of claim 14, wherein the oxidizing agent is positioned on a tray near the bottom of the distillation column.

Embodiment 16

The system of claim 14 or claim 15, wherein the oxidizing agent is positioned in the sump at the bottom of the distillation column.

Embodiment 17

The system of any of claims 14-16, wherein the acetic acid feed line is positioned to feed acetic acid into the sump at the bottom of the distillation column.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

Unless otherwise specified herein, any reference to standards, regulations, testing methods and the like, such as ASTM D1003, ASTM D4935, ASTM 1746, FCC part 18, CISPR11, and CISPR 19 refer to the standard, regulation, guidance or method that is in force at the time of filing of the present application.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the disclosed subject matter is not intended to be limited to the particular embodiments described in the specification. Accordingly, the appended claims are intended to include within their scope such alternatives.

The invention claimed is:

1. A process for purifying acetic acid, comprising:
feeding a feed stream comprising acetic acid into a bottom half of a distillation column;
distilling the acetic acid in the presence of a heterogeneous oxidizing agent in the distillation column to oxidize oxidizable impurities in the acetic acid, wherein the heterogeneous oxidizing agent is capable of cleaving C=C bonds; and
removing a distilled acetic acid stream from the distillation column,
wherein the heterogeneous oxidizing agent is positioned in the feed stream.

2. The process of claim 1, wherein the oxidizable impurities comprise an α,β-unsaturated carbonyl compound.

3. The process of claim 2, wherein the α,β-unsaturated carbonyl compound comprises an α,β-unsaturated carboxylic acid.

4. The process of claim 3, wherein the α,β-unsaturated carboxylic acid comprises acrylic acid.

5. The process of claim 1, wherein the distillation column comprises a sump in the bottom half of the distillation column and the heterogeneous oxidizing agent is positioned in the sump.

6. The process of claim 1, wherein the heterogeneous oxidizing agent comprises potassium permanganate.

7. The process of claim 6, wherein the distillation column comprises an aqueous solution of potassium permanganate.

8. The process of claim 6, wherein the potassium permanganate comprises potassium permanganate on a solid support.

9. The process of claim 8, wherein the solid support is silica.

10. The process of claim 1, wherein the process further comprises feeding the distilled acetic acid stream through a sorbent phase capable of removing at least one impurity selected from water, or formic acid, or aldehydes.

11. The process of claim 1, wherein the process further comprises additional distillation of acetic acid through an additional distillation column.

12. A process for purifying acetic acid, comprising:
feeding a feed stream comprising acetic acid into a distillation column, and
distilling the acetic acid in the presence of a heterogeneous oxidizing agent,
wherein:
the distillation column comprises:
a top half and a bottom half; and a sump in the bottom half of the distillation column; and wherein the feed stream is fed into the bottom half of the distillation column; and wherein the heterogeneous oxidizing agent is positioned in the feed stream.

13. The process of claim 12, wherein the heterogeneous oxidizing agent comprises potassium permanganate.

14. The process of claim 13, wherein the distillation column comprises an aqueous solution of potassium permanganate.

15. The process of claim 13, wherein the potassium permanganate comprises potassium permanganate on a solid support.

* * * * *